United States Patent [19]

Hausberg et al.

[11] 4,376,123

[45] Mar. 8, 1983

[54] HEXAHYDROAZEPINYLOXY-CHROMONES USEFUL AS ANTIDEPRESSANTS

[75] Inventors: Hans-Heinrich Hausberg, Weiterstadt; Helmut Prücher, Heppenheim; Jürgen Uhl, Seeheim; Christoph Seyfried, Seeheim-Jugenheim; Klaus Minck, Ober-Ramstadt, all of Fed. Rep. of Germany

[73] Assignee: Merck Patent Gesellschaft mit Beschrankter Haftung, Darmstadt, Fed. Rep. of Germany

[21] Appl. No.: 216,454

[22] Filed: Dec. 15, 1980

[30] Foreign Application Priority Data

Dec. 13, 1979 [DE] Fed. Rep. of Germany ....... 2950135

[51] Int. Cl.$^3$ .................. A61K 31/35; C07D 311/24; C07D 311/30; C07D 311/36
[52] U.S. Cl. .................................. 424/283; 549/401; 549/403; 546/196; 546/197; 546/206; 564/352; 564/355
[58] Field of Search ......... 260/345.2, 239 B, 340.5 R, 260/345.5; 546/206, 196, 197; 564/352, 355; 424/283; 549/401, 403

[56] References Cited

U.S. PATENT DOCUMENTS 3,476,767 11/1969 Bencze ............................ 260/239 B
3,637,718 1/1972 Krämer et al. ..................... 546/196
4,194,009 3/1980 Molloy et al. ...................... 564/352

FOREIGN PATENT DOCUMENTS 1357633 6/1974 United Kingdom ............. 260/345.2

OTHER PUBLICATIONS

Joullie et al., Chem. Abstract, 82, 72789e (1975) (Abstract of Ger. Offen. 2,413,605).
Journal für Praktische Chemie, vol. 311, pp. 183-186 (1969).

Primary Examiner—Nicky Chan
Attorney, Agent, or Firm—Millen & White

[57] ABSTRACT

Basic ethers of the formula

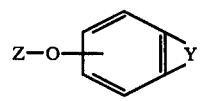

wherein Z is $CH_3$—$NR^2$—$CH_2CH_2$—$CHR^1$—, (1-$R^2$-3-piperidyl)-$CHR^3$—, (1-$R^2$-2-piperidyl)-$CH_2$—$CHR^3$- or 1-$R^2$-3-$R^4$-hexahydroazepinyl; $R^1$ is cyclopropyl or Ar; $R^2$ is H, alkyl of 1-4 C atoms, alkenyl of 2-4 C atoms, cycloalkylalkyl of 4-8 C atoms or benzyl; $R^3$ is H or Ar; $R^4$ is H or alkyl of 1-4 C atoms, Y is —O—CH-$Q^1$—$CHQ^2$—$CH_2$—, —O—$CHQ^1$—$CHQ^2$—CO—, —O—$CQ^1$=$CQ^2$—CO— or —$CH_2$—$CHQ^1$—CH-$Q^2$—CO—; $Q^1$ and $Q^2$ are independently each H, alkyl of 1-4 C atoms, cycloalkyl or alkylcycloalkyl each of 3-6 total C atoms or Ar; and Ar is phenyl or phenyl substituted by F, Cl, alkoxy or alkylthio, each of 1-4 C atoms, methylenedioxy or $CF_3$; with the proviso that when Z is $(CH_3)_2N$—$CH_2CH_2$—$CHR^1$ in 7-position and Y is —O—$C(C_6H_5)$=CH—CO— or —O—$C(C_6H_5)$=$C(CH_3)$—CO—, $R^1$ is cyclopropyl, or phenyl substituted by F, Cl, alkoxy or alkylthio, each of 1-4 C atoms, methylenedioxy or $CF_3$;

or a physiologically acceptable acid addition salt thereof, have valuable pharmacological properties, e.g., are antidepressants.

4 Claims, No Drawings

HEXAHYDROAZEPINYLOXY-CHROMONES USEFUL AS ANTIDEPRESSANTS

BACKGROUND OF THE INVENTION

The present invention relates to new basic ethers having valuable pharmacological properties.

Certain related compounds are known from the Journal für praktische Chemie, Volume 311, pages 183 to 186 (1969), in particular 7-(1-phenyl-3-dimethylaminopropoxy)-flavone and 3-methyl-7-(1-phenyl-3-dimethylaminopropoxy)-flavone. However, it is stated in this reference that the disclosed substances exhibit "no pharmacodynamically usable properties". In light of this statement, the valuable pharmacological properties of the present new compounds are particularly surprising.

SUMMARY OF THE INVENTION

It is an object of this invention to provide new compounds which can be used for the preparation of medicaments.

Upon further study of the specification and appended claims, further objects and advantages of this invention will become apparent to those skilled in the art.

These objects have been attained by providing new basic ethers of Formula I

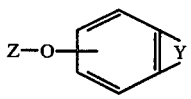

wherein Z is $CH_3-NR^2-CH_2CH_2-CHR^1-$, (1-$R^2$-3-piperidyl)-$CHR^3-$, (1-$R^2$-2-piperidyl)-$CH_2-CH-R^3-$ or 1-$R^2$-3-$R^4$-4-hexahydroazepinyl; $R^1$ is cyclopropyl or Ar; $R^2$ is H, alkyl of 1–4 C atoms, alkenyl of 2–4 C atoms, cycloalkylalkyl of 4–8 C atoms or benzyl; $R^3$ is H or Ar; $R^4$ is H or alkyl of 1–4 C atoms; Y is $-O-CHQ^1-CHQ^2-CH_2-$, $-O-CHQ^1-CHQ^2-CO-$, $-O-CQ^1=CQ^2-CO-$ or $-CH_2-CHQ^1-CHQ^2-CO-$; $Q^1$ and $Q^2$ are independently each H, alkyl of 1–4 C atoms, cycloalkyl of 3–6 C atoms or Ar; and Ar is phenyl or phenyl substituted by F, Cl, alkoxy or alkylthio, each of 1–4 C atoms, methylenedioxy or $CF_3$; with the proviso that when Z is $(CH_3)_2N-CH_2CH_2-CHR^1$ in 7-position and Y is $-O-C(C_6H_5)=CH-CO-$ or $-O-C(C_6H_5)=C(CH_3)-CO-$, $R^1$ is cyclopropyl or phenyl which is substituted by F, Cl, alkoxy or alkylthio each of 1–4 C atoms, methylenedioxy or $CF_3$;

and the physiologically acceptable acid addition salts thereof.

DETAILED DISCUSSION

The invention relates to the basic ethers of Formula I and to their physiologically acceptable acid addition salts.

In $R^2$, $R^4$, $Q^1$ and $Q^2$, alkyl is preferably methyl, and also ethyl, n-propyl, isopropyl, n-butyl, isobutyl, sec-butyl or tert-butyl. Cycloalkyl (in the radicals $Q^1$ and $Q^2$) is preferably cyclopropyl, cyclobutyl, cyclopentyl or cyclohexyl and also 1-methylcyclopropyl, 2-methylcyclopropyl, 1-, 2- or 3-methylcyclobutyl, 1-, 2- or 3-methylcyclopentyl, 1-ethylcyclopropyl or 2-ethylcyclopropyl and the like. Alkoxy (in the radical Ar) is preferably methoxy and also ethoxy, n-propoxy, isopropoxy, n-butoxy, isobutoxy, sec-butoxy or tert-butoxy. Alkenyl (in the radical $R^2$) is preferably allyl and is also vinyl, propenyl, isopropenyl, 1-butene-1-yl, 1-butene-2-yl, 2-butene-1-yl, 2-butene-2-yl, 3-butene-1-yl, 3-butene-2-yl, 2-methyl-1-propene-1-yl, 2-methyl-1-propene-2-yl or 2-methyl-2-propene-1-yl. Cycloalkylalkyl (in the radical $R^2$) is preferably cyclopropylmethyl, but is also, for example, 1-cyclopropylethyl, 2-cyclopropylethyl, 1-, 2- or 3-cyclopropylpropyl, 1-cyclopropyl-1-methylethyl, 1-, 2-, 3- or 4-cyclopropylbutyl, 1-cyclopropyl-1-methylpropyl, 1-, 2-, 3-, 4- or 5-cyclopropylpentyl, cyclobutylmethyl, 1-cyclobutylethyl, 2-cyclobutylethyl, 1-, 2- or 3-cyclobutylpropyl, 1-, 2-, 3- or 4-cyclobutylbutyl, cyclopentylmethyl, 1-cyclopentylethyl, 2-cyclopentylethyl, 1-, 2- or 3-cyclopentylpropyl, cyclohexylmethyl, 1-cyclohexylethyl, 2-cyclohexylethyl or cycloheptylmethyl. Alkylthio (in the radical Ar) is preferably methylthio, but is also ethylthio, n-propylthio, isopropylthio, n-butylthio, isobutylthio, sec-butylthio or tert-butylthio.

The radical Ar is preferably phenyl and secondarily p-fluorophenyl, p-chlorophenyl, p-methoxyphenyl, 3,4-methylenedioxyphenyl or m-trifluoromethylphenyl, and also o-fluorophenyl, m-fluorophenyl, o-chlorophenyl, m-chlorophenyl, o-methoxyphenyl, m-methoxyphenyl, o-, m- or p-methylthiophenyl, 2,3-methylenedioxyphenyl, o-trifluoromethylphenyl or p-trifluoromethylphenyl. If several radicals Ar are present in the same molecule, they can be identical or different from one another.

In detail, $R^1$ is preferably phenyl, p-fluorophenyl, p-chlorophenyl or p-methoxyphenyl; $R^2$ is preferably H or methyl and secondarily is preferably ethyl, allyl, cyclopropylmethyl or benzyl; $R^3$ is preferably H or phenyl; and $R^4$ is preferably H or methyl.

Accordingly, the radical Z is preferably 1-phenyl-3-dimethylaminopropyl and secondarily is preferably 1-phenyl-3-methylaminopropyl, 1-phenyl-3-N-benzyl-N-methylaminopropyl, (3-piperidyl)-methyl, α-(3-piperidyl)-benzyl, (1-methyl-3-piperidyl)-methyl, α-(1-methyl-3-piperidyl)-benzyl, 2-(2-piperidyl)-ethyl, 1-phenyl-2-(2-piperidyl)-ethyl, 2-(1-methyl-2-piperidyl)-ethyl, 1-phenyl-2-(1-methyl-2-piperidyl)-ethyl, 4-hexahydroazepinyl, 1-methyl-4-hexahydroazepinyl, 3-methyl-4-hexahydroazepinyl and 1,3-dimethyl-4-hexahydroazepinyl, and also, for example, 1-phenyl-3-methylethylaminopropyl, 1-phenyl-3-(N-methyl-N-allylamino)-propyl, 1-phenyl-3-(N-methyl-N-cyclopropylmethylamino)-propyl, (1-ethyl-3-piperidyl)-methyl, α-(1-ethyl-3-piperidyl)-benzyl, (1-allyl-3-piperidyl)-methyl, α-(1-allyl-3-piperidyl)-benzyl, (1-cyclopropylmethyl-3-piperidyl)-methyl, α-(1-cyclopropylmethyl-3-piperidyl)-benzyl, (1-benzyl-3-piperidyl)-methyl, α-(1-benzyl-3-piperidyl)-benzyl, 2-(1-ethyl-2-piperidyl)-ethyl, 1-phenyl-2-(1-ethyl-2-piperidyl)-ethyl, 2-(1-allyl-2-piperidyl)-ethyl, 1-phenyl-2-(1-allyl-2-piperidyl)-ethyl, 2-(1-cyclopropylmethyl-2-piperidyl)-ethyl, 1-phenyl-2-(1-cyclopropylmethyl-2-piperidyl)-ethyl, 2-(1-benzyl-2-piperidyl)-ethyl, 1-phenyl-2-(1-benzyl-2-piperidyl)-ethyl, 3-ethyl-4-hexahydroazepinyl, 1-methyl-3-ethyl-4-hexahydroazepinyl, 1-ethyl-4-hexahydroazepinyl, 1-allyl-4-hexahydroazepinyl, 1-cyclopropylmethyl-4-hexahydroazepinyl or 1-benzyl-4-hexahydroazepinyl, 1-cyclopropyl-3-methylaminopropyl, 1-p-fluorophenyl-3-methylaminopropyl, 1-p-chlorophenyl-3-methylaminopropyl, 1-m-trifluoromethylphenyl-3-methylaminopropyl, 1-cyclopropyl-3-dimethylaminopropyl, 1-p-fluorophenyl-3-dimethylaminopropyl, 1-p-chlorophenyl-3-dimethylaminopropyl or 1-m-trifluoromethylphenyl-3-dimethylaminopropyl.

The radicals $Q^1$ and $Q^2$ can be identical or different. Preferably one of these radicals is H or alkyl of 1–3 C atoms and the other is H or Ar, Ar being, in particular, phenyl, p-fluorophenyl, p-chlorophenyl, p-methoxyphenyl, 3,4-methylenedioxyphenyl or m-trifluoromethylphenyl.

The radical Y is, accordingly, preferably —O—CHQ³—CHQ⁴—CH₂— (wherein the radicals $Q^3$ and $Q^4$ are each H or alkyl of 1–3 C atoms, but one of these radicals preferably is H; chromans), —O—CHAr—CHQ⁴—CH₂— (flavans), —O—CHQ³—CHAr—CH₂— (iso-flavans), —O—CHQ³—CHQ⁴—CO— (chromanones), —O—CHAr—CHQ⁴—CO— (flavanones), —O—CHQ³—CHAr—CO— (iso-flavanones), —O—CQ³=CQ⁴—CO— (chromones), —O—CAr=CQ⁴—CO— (flavones), —O—CQ³=CAr—CO— (isoflavones) or —CH₂—CHQ³—CHQ⁴—CO— (tetralones). Among these, the isoflavones are particularly preferred and secondarily the tetralones and the flavones.

Accordingly, the invention relates particularly to those compounds of the Formula I in which at least one of the mentioned radicals has one of the meanings indicated above, especially one of the preferred meanings indicated above. Some preferred groups of compounds can be expressed by means of the partial Formulae Ia to Ic which follow, which correspond to the Formula I, and wherein the radicals not designated in greater detail have the meanings indicated for Formula I, but wherein: in Ia: Z is CH₃—NR²—CH₂CH₂—CHR¹—; $R^1$ is phenyl; $R^2$ is H, methyl or benzyl; Y is —O—CH₂CH₂CH₂—, —O—CHAr—CH₂CH₂—, —O—CH₂—CH(C₆H₅)—CH₂—, —O—CH₂CH₂—CO—, —O—CHAr—CHQ⁴—CO—, —O—CAr=CQ⁴—CO—, —O—CH=CAr—CO— or —CH₂CH₂CH₂—CO—, Ar is phenyl, p-fluorophenyl, p-chlorophenyl, p-methoxyphenyl, 3,4-metylenedioxyphenyl or m-trifluoromethylphenyl; and $Q^4$ is H or alkyl of 1–3 C atoms; in Ib: Z is CH₃—NR²—CH₂CH₂—CHR¹; $R^1$ is phenyl; $R^2$ is H, methyl or benzyl; and Y is —O—C(C₆H₅)=CH—CO—, —O—CH=C(C₆H₅)—CO— or —CH₂CH₂CH₂—CO—; and in Ic: Z is CH₃—NR²—CH₂CH₂—CHR¹—; $R^1$ is phenyl; $R^2$ is H, methyl or benzyl; and Y is —O—CH=C(C₆H₅)—CO—.

The compounds of Formula I can contain one or more asymmetric carbon atoms. They can therefore exist in the form of racemates and, if several asymmetric carbon atoms are present, also in the form of mixtures of several racemates, as well as in various optically active forms.

The present invention relates further to a process for preparing the compounds of Formula I and their physiologically acceptable acid addition salts, comprising reacting a phenol of Formula II

HO—G                II wherein G is the group

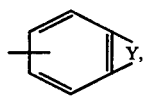

or one of its salts, with an amine of Formula III

Z—X                III wherein X is Cl, Br, I or OH and Z is as defined above, or with one of its reactive derivatives; and, if appropriate, in a resulting compound of Formula I, converting a secondary amino group by treatment with an alkylating, alkenylating, cycloalkylating or benzylating agent into the corresponding tertiary amino group, or converting an N-benzyl group by treatment with a reducing agent into an NH group, and/or converting a resulting base of Formula I by treatment with an acid into one of its physiologically acceptable acid addition salts.

The preparation of the compounds of Formula I is effected in other respects in accordance with methods which are in themselves known such as are described in the literature (for example in the standard works such as Houben-Weyl, Methoden der Organischen Chemie ("Methods of Organic Chemistry"), Georg-Thieme-Verlag, Stuttgart; or Organic Reactions, John Wiley and Sons, Inc., New York) and, in particular, under reaction conditions such as are known and suitable for these reactions. In these reactions it is also possible to make use of variants which are in themselves known, but are not described in greater detail herein.

The starting materials of Formulae II and III can, if desired, also be formed in situ, in such a way that they are not isolated from the reaction mixture, but are immediately reacted further to produce the compounds of Formula I.

The phenols of Formula II are in most cases known. When they are new, they can be prepared by methods which are in themselves known, for example by splitting corresponding benzyl or methyl ethers.

In the bases of Formula III, the radical X is preferably Cl or Br. Reactive derivatives of these bases include, in particular, the reactive esters of the alcohols of Formula III (X=OH), preferably the corresponding alkylsulfonates (wherein the alkyl group is of 1–6 C atoms) and the corresponding arylsulfonates (wherein the aryl group is of 6–10 C atoms), for example the corresponding methanesulfonates, benzenesulfonates, p-toluenesulfonates, naphthalene-1-sulfonates or naphthalene-2-sulfonates.

Some of the bases of Formula III are known. Those bases of Formula III which have not been disclosed hitherto can be prepared by methods which are in themselves known in analogy to their use with known compounds. Thus the compounds of Formula III (X=OH) can be obtained, for example, by reducing corresponding esters or ketones of the type CH₃—NR²—CH₂CH₂—CO—R¹, (1-R²-3-piperidyl)-COO-alkyl, (1-R²-3-piperidyl)-CO—R³, (1-R²-2-piperidyl)-CH₂—COO-alkyl, (1-R²-2-piperidyl)-CH₂—CO—R³ or 1-R²-3-R⁴-hexahydroazepin-4-one, while the compounds of Formula III (X=Cl, Br or I) can be obtained from the alcohols by means of inorganic halides, such as SOCl₂, PBr₃ or HI, and the sulfonates can be obtained by esterifying the alcohols with the corresponding sulfonyl chlorides. The tertiary amines among those of Formula III (in which $R^2$ is not H) are also accessible from the secondary amines (III, $R^2$=H) by alkylation, alkenylation, cycloalkylalkylation or benzylation. Conversely, the secondary amines (III, $R^2$=H) can be obtained from the corresponding N-alkyl derivatives (III, $R^2$=alkyl having 1–4 C atoms) by dealkylation by means of chloroformic acid ethyl ester. Furthermore, the amines of Formula III can be prepared by reducing corresponding pyridines or azepines. Thus, for example, it is possible to metallize 2-methylpyridine with $C_6H_5Li$, subsequently to react the product with benzaldehyde to give 1-phenyl-2-(2-pyridyl)-ethanol and to reduce the latter to give 1-phenyl-2-(2-piperidyl)-ethanol. 1-Methyl-4-hydroxy-hexahydroazepine is accessible by ring enlargement of 1-methyl-4-piperidone by means of $CH_2N_2$ to give 1-methyl-hexahydroazepin-4-one and reduction of the latter using $NaBH_4$.

Before the reaction with III, the phenol II is preferably first converted into a salt, particularly into a metal salt, for example an alkali metal salt (Li, Na or K salt) or a thallium salt. The phenol can be reacted with a reagent which forms metal salts, for example an alkali metal (for example Na), an alkali metal hydride or amide (for example LiH, NaH, $NaNH_2$ or $KNH_2$), a metal alcoholate (wherein the alcohol part preferably has 1-4 C atoms, for example lithium methylate, ethylate or tert-butylayte, sodium methylate, ethylate or tert-butylate, potassium methylate, ethylate or tert-butylate or thallium methylate, ethylate or tert-butylate), an organometallic compound (for example butyllithium, phenyllithium or phenylsodium) or a metal hydroxide, carbonate or bicarbonate (for example of Li, Na, K or Ca). The preparation of the phenolate is advantageously effected in the presence of a solvent or mixture of solvents. Examples of suitable solvents are hydrocarbons (such as hexane, benzene, toluene or xylene), halogenated hydrocarbons (such as $CH_2Cl_2$, $CHCl_3$ or $CCl_4$), ethers (such as diethyl ether, diisopropyl ether, tetrahydrofuran (THF), dioxane or diethylene glycol dimethyl ether), amides, such as dimethylformamide (DMF), alcohols (such as methanol or ethanol) or ketones (such as acetone or butanone).

The phenol II, or its salt, is preferably reacted with the amine III in the presence of a diluent, for example the solvent which has been used for the preparation of the salt, but this can be replaced by another solvent or diluted with another solvent. A particular variant consists in carrying out the reaction in two phases (for example in $CH_2Cl_2$/aqueous sodium hydroxide solution), in which case it is also possible to add a catalyst (for example a crown ether, an ammonium salt, such as a trialkylbenzylammonium halide or a phosphonium salt). The reaction is generally carried out at temperatures of about $-20°$ to $180°$ C., preferably $20°$ to $160°$ C.

The phenolate can also be formed in situ. In this case the phenol II and the amine III are allowed to react with one another in the presence of a base.

A variant of the reaction consists in reacting a phenol of Formula II with a hydroxyamine of Formula III (X=OH) in the presence of a dehydrating agent, for example an azodicarboxylic acid dialkyl ester, in the presence of triphenylphosphine in an inert solvent, such as THF, at about $-10°$ to $+30°$ C.

Furthermore, it is possible, if desired, to alkylate a resulting secondary amine of Formula I ($R^2$=H) on the nitrogen atom, in which case tertiary amines of Formula I ($R^2$=alkyl having 1-4 C atoms) are obtained. Examples of suitable N-alkylating agents are the corresponding alkyl halides, for example methyl chloride, methyl bromide, methyl iodide, ethyl chloride, ethyl bromide, ethyl iodide and n-propyl chloride, bromide or iodide and the like, and also the corresponding dialkyl sulfates, such as dimethyl sulfate, and the corresponding sulfonic acid alkyl esters, such as p-toluenesulfonic acid methyl ester. A methyl group can also be introduced, for example by treatment with formic acid and aqueous formaldehyde solution, preferably by heating for several hours at temperatures of $50°$ to $100°$ C. In general, the N-alkylation is preferably effected in the presence or absence of an inert solvent at temperatures of about $0°$ to about $120°$ C., preferably of $40°$ to $100°$ C., and it is also possible for a catalyst to be present, preferably a base such as potassium tert-butylate.

It is also possible to carry out alkylation by treating a secondary base I ($R^2$=H) with an aldehyde or ketone in the presence of hydrogen and a hydrogenation catalyst (for example Raney nickel) at temperatures of about $50°$ to $100°$ C. and pressures of about 1 to 200 atmospheres; thus, using acetone, the corresponding isopropyl compound I ($R^2$=isopropyl) is obtained.

It is also possible to carry out alkylation in several stages. For example, a compound of Formula I ($R^2$=H) can first be acylated in a manner which is in itself known (for example acylated by treatment with acetic anhydride/pyridine) and the resulting N-acylation product (for example N-acetylation product) can then be reduced to give the desired tertiary amine, for example by means of a complex metal hydride, such as $LiAlH_4$, in an inert solvent, such as diethyl ether or THF, preferably at temperatures of $20°$ to $60°$ C.

A secondary amine of Formula I ($R^2$=H) can be treated in a completely analogous manner with alkenylating, cycloalkylalkylating or benzylating agents (for example alkenyl halides, such as allyl chloride or bromide, cyclopropylmethyl halides, such as cyclopropylmethyl chloride or bromide, or benzyl halides, such as benzyl chloride or bromide), in which case compounds of Formula I ($R^2$=alkenyl of 2-4 C atoms, cycloalkylalkyl of 4-8 C atoms or benzyl) are formed.

Furthermore, in a compound of Formula I ($R^2$=benzyl), the benzyl group can be removed by reduction by a method indicated in the literature, preferably by hydrogenolysis in the presence of a noble metal catalyst or with the aid of a dealkylating agent, for example $ClCOOC_2H_5$/NaOH.

A resulting base of Formula I can be converted by means of an acid into the appropriate acid addition salt. Acids suitable for this reaction are those which provide physiologically acceptable salts. Thus it is possible to use inorganic acids, for example sulfuric acid, hydrogen halide acids, such as hydrochloric acid or hydrobromic acid, phosphoric acids, such as orthophosphoric acid, nitric acid or sulfamic acid, and also organic acids, in particular aliphatic, alicyclic, araliphatic, aromatic or heterocyclic monobasic or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicyclic acid, 2-phenylpropionic acid, citric acid, gluconic acid, ascorbic acid, nicotinic acid, isonicotinic acid, methanesulfonic acid, ethanesulfonic acid, ethanedisulfonic acid, 2-hydroxyethanesulfonic acid, benzene-sulfonic acid, p-toluenesulfonic acid, naphthalenemonosulfonic acid, naphthalenedisulfonic acid and lauryl-sulfuric acid.

The free bases of Formula I can, if desired, be liberated from their salts by treatment with strong bases, such as sodium hydroxide or carbonate or potassium hydroxide or carbonate.

It has been found that the compounds of Formula I and their physiologically acceptable acid addition salts possess valuable pharmacological properties. Thus they exhibit, in particular, effects on the central nervous system, above all anti-depressant activity. In detail, it is possible to demonstrate a reserpine-antagonistic action (which can be detected, for example on mice, in respect of reserpine, by a technique modeled on the method of Askew, Life Science, Volume 10 (1963), pages 725-730), an anticataleptic action (which can be detected, for example on rats, in respect of tetrabenazine, by a technique modeled on the method of Giurgea et al., Medicina Experimentalis, Volume 9, (1963), pages 249-262) and an antiptotic action (which can be detected, for example in respect of reserpine, by a technique modeled on the methodology of Domenjoz and Theobald, Arch. int. pharmacodyn., Volume 120 (1959), pages 450 et seq., using the evaluation according to Rubin et al., J. Pharmacol. Exp. Therap., Volume 120 (1957), pages 125-136). Furthermore, the action of 5-hydroxy-tryptophan in mice (method similar to that of Ross et al., Acta pharmacol. et toxicol., Volume 39 (1976), pages 152-166) can be potentiated, and the effects on the central nervous system of excitation and increase in temperature, which can be initiated by D-amphetamine sulfate (for example 1.5 mg/kg administered subcutaneously 1 hour after the test substance, which is also administered subcutaneously) and aggregation (putting 5 rats together in a glass container) (methodology according to Müller-Calgan et al., in Zippel, H. P. (Ed.): Memory and Transfer of Information, Plenum Press, New York-London, 1973, pages 87-125), can be increased and/or prolonged. The substances have an effect on the biogenous amines of CNS. Thus, for example, in vitro they lead to inhibition of the absorption of nor-adrenalin, 5-hydroxytryptamine and dopamine (methodology: Kannegiesser et al., Biochem. Pharmacol., Volume 22 (1973), pages 73-84) in synaptosomes, and in vivo they inhibit the liberation, within the brain, of catecholamine and serotonin which is induced by tyramine derivatives (methodology: Carlsson et al., Europ. J. Pharmacol., Volume 5 (1969), pages 357-366; 367-373). A hypotensive action and a spasmolytic action are also produced, and these can be determined by methods in current use for this purpose.

Compounds of Formula I and their physiologically acceptable acid addition salts can, therefore, be used as medicinally active compounds and also as intermediate products for the preparation of other medicinally active compounds.

Thus, the invention further relates to the use of the compounds of Formula I and their physiologically acceptable salts for the preparation of pharmaceutical formulations, particularly by a non-chemical route. In this connection they can be brought into a suitable dosage form together with at least one excipient or adjuvant and, if appropriate, in combination with one or more other active compound(s).

The present invention further relates to agents, especially pharmaceutical formulations, containing a compound of Formula I and/or one of its physiologically acceptable acid addition salts. These formulations can be employed as medicaments in human or veterinary medicine. Suitable excipients are organic or inorganic substances which are suitable for enteral (for example oral) or parenteral administration or for local application, and which do not react with the new compounds, for example water, vegetable oils, benzyl alcohols, polyethylene glycols, gelatines, carbohydrates, such as lactose or starch, magnesium stearate, talc or petroleum jelly. Tablets, dragees, capsules, syrups, elixirs, drops or suppositories are especially used for enteral administration; solutions, preferably oily or aqueous solutions, and also suspensions, emulsions or implants are especially used for parenteral administration; and ointments, creams or powders are especially used for topical application. The new compounds can also be lyophilized and the resulting lyophilizates can be used, for example, for the preparation of injection preparations. The formulations indicated can be sterilized and/or can contain adjuvants, such as lubricants, preservatives, stabilizing agents and/or wetting agents, emulsifiers, salts for regulating the osmotic pressure, buffer substances, colorants, flavoring substances and/or aroma generating substances. If desired, they can also contain one or more additional active compounds, for example one or more vitamins.

The invention further relates to the use of the compounds of Formula I and their physiologically acceptable acid addition salts in combating diseases, particularly depressions of various etiologies and symptomatologies, and to their use in the therapeutic treatment of the human or animal body.

In this connection, the substances of this invention are generally administered in a manner analogous to that of known psychopharmacological agents which are commercially available (for example Imipramine), preferably in dosages of about 2-500 mg, particularly of 10-50 mg, per dosage unit. The daily dosage is preferably about 0.05 to 10 mg/kg of body weight. The particular dose for each specific patient depends, however, on a very wide variety of factors, for example on the activity of the particular compound employed, on the age, body weight, general state of health, sex, and diet of the patient, on the time and route of administration, on the excretion rate and combination of medicaments and on the severity of the particular disease to which the therapy applies. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Each of the compounds of Formula I mentioned in the examples which follow is particularly suitable for the preparation of pharmaceutical formulations.

In the following examples, "customary working-up" denotes:

Water is added if necessary, the mixture is extracted with an organic solvent, such as benzene, chloroform or methylene chloride, the phases are separated and the organic phase is dried over sodium sulfate, the mixture is filtered, the filtrate is evaporated and the product is purified by chromatography and/or crystallization.

The Rf values were obtained on silica gel using 8:2 toluene/triethylamine, unless otherwise indicated.

EXAMPLE 1

A solution of 23.8 g of 7-hydroxyisoflavone in 250 ml of 0.5 N ethanolic KOH is evaporated, the residue is dissolved in 200 ml of DMF and the solution is heated to 150°; a solution of 20 g of 1-chloro-1-phenyl-3-dimethylaminopropane in 50 ml of DMF is added, while stirring. The mixture is stirred for 1.5 hours at 150° and 7-(1-phenyl-3-dimethylaminopropoxy)-isoflavone is precipitated by adding water. M.p. 128°–130° (from acetone). Hydrochloride, m.p. 259°–260°.

EXAMPLES 2 TO 220

The following are obtained analogously to Example 1 by etherifying the Na salts of 6-hydroxychroman, 7-hydroxychroman, 6-hydroxyflavan, 7-hydroxyflavan, 6-hydroxyisoflavan, 7-hydroxyisoflavan, 6-hydroxychromanone, 7-hydroxychromanone, 6-hydroxyflavanone, 7-hydroxyflavanone, 6-hydroxyisoflavanone, 7-hydroxyisoflavanone, 6-hydroxychromone, 7-hydroxychromone, 5-, 6-, 7- or 8-hydroxyflavone, 5-, 6-, 7- or 8-hydroxyisoflavone or 5-, 6- or 7-hydroxytetralone with 1-chloro-1-phenyl-3-methylaminopropane, 1-chloro-1-phenyl-3-dimethylaminopropane, 1-chloro-1-phenyl-3-N-benzyl-N-methylaminopropane, 3-chloromethylpiperidine, 3-(α-chlorobenzyl)-piperidine, 1-methyl-3-chloromethylpiperidine, 1-methyl-3-(α-chlorobenzyl)-piperidine, 2-(2-chloroethyl)-piperidine, 2-(2-chloro-2-phenylethyl)-piperidine, 1-methyl-2-(2-chloroethyl)-piperidine, 1-methyl-2-(2-chloro-2-phenylethyl)-piperidine, 1-benzyl-2-(2-chloroethyl)-piperidine, 4-chlorohexahydroazepine, 1-methyl-4-chlorohexahydroazepine, 3-methyl-4-chlorohexahydroazepine and 1,3-dimethyl-4-chlorohexahydroazepine or the corresponding bromine compounds:

2. 6-(1-Phenyl-3-methylaminopropoxy)-chroman, hydrochloride, m.p. 164°.
3. 7-(1-Phenyl-3-methylaminopropoxy)-chroman.
4. 6-(1-Phenyl-3-dimethylaminopropoxy)-chroman, hydrochloride, m.p. 137°–139°.
5. 7-(1-Phenyl-3-dimethylaminopropoxy)-chroman, hydrochloride, m.p. 182°–183°.
6. 6-(1-Phenyl-3-N-benzyl-N-methylaminopropoxy)-chroman, hydrochloride, m.p. 139°–140°.
7. 7-(1-Phenyl-3-N-benzyl-N-methylaminopropoxy)-chroman.
8. 6-[α-(1-Methyl-3-piperidyl)-benzyloxy]-chroman.
9. 7-[α-(1-Methyl-3-piperidyl)-benzyloxy]-chroman.
10. 6-[2-(1-Methyl-2-piperidyl)-ethoxy]-chroman, hydrochloride, m.p. 100°–103°.
11. 7-[2-(1-Methyl-2-piperidyl)-ethoxy]-chroman.
12. 6-(1,3-Dimethyl-4-hexahydroazepinyloxy)-chroman.
13. 7-(1,3-Dimethyl-4-hexahydroazepinyloxy)-chroman.
14. 6-(1-Phenyl-3-methylaminopropoxy)-flavan.
15. 7-(1-Phenyl-3-methylaminopropoxy)-flavan.
16. 6-(1-Phenyl-3-dimethylaminopropoxy)-flavan.
17. 7-(1-Phenyl-3-dimethylaminopropoxy)-flavan.
18. 6-(1-Phenyl-3-N-benzyl-N-methylaminopropoxy)-flavan.
19. 7-(1-Phenyl-3-N-benzyl-N-methylaminopropoxy)-flavan.
20. 6-[α-(1-Methyl-3-piperidyl)-benzyloxy]-flavan.
21. 7-[α-(1-Methyl-3-piperidyl)-benzyloxy]-flavan.
22. 6-[2-(1-Methyl-2-piperidyl)-ethoxy]-flavan.
23. 7-[2-(1-Methyl-2-piperidyl)-ethoxy]-flavan.
24. 6-(1,3-Dimethyl-4-hexahydroazepinyloxy)-flavan.
25. 7-(1,3-Dimethyl-4-hexahydroazepinyloxy)-flavan.
26. 6-(1-Phenyl-3-methylaminopropoxy)-isoflavan.
27. 7-(1-Phenyl-3-methylaminopropoxy)-isoflavan.
28. 6-(1-Phenyl-3-dimethylaminopropoxy)-isoflavan.
29. 7-(1-Phenyl-3-dimethylaminopropoxy)-isoflavan, m.p. 98°–100°.
30. 6-(1-Phenyl-3-N-benzyl-N-methylaminopropoxy)-isoflavan.
31. 7-(1-Phenyl-3-N-benzyl-N-methylaminopropoxy)-isoflavan.
32. 6-[α-(1-Methyl-3-piperidyl)-benzyloxy]-isoflavan.
33. 7-[α-(1-Methyl-3-piperidyl)-benzyloxy]-isoflavan.
34. 6-[2-(1-Methyl-2-piperidyl)-ethoxy]-isoflavan.
35. 7-[2-(1-Methyl-2-piperidyl)-ethoxy]-isoflavan.
36. 6-(1,3-Dimethyl-4-hexahydroazepinyloxy)-isoflavan.
37. 7-(1,3-Dimethyl-4-hexahydroazepinyloxy)-isoflavan.
38. 6-(1-Phenyl-3-methylaminopropoxy)-chromanone.
39. 7-(1-Phenyl-3-methylaminopropoxy)-chromanone.
40. 6-(1-Phenyl-3-dimethylaminopropoxy)-chromanone, hydrochloride, m.p. 188°–191°.
41. 7-(1-Phenyl-3-dimethylaminopropoxy)-chromanone.
42. 6-(1-Phenyl-3-N-benzyl-N-methylaminopropoxy)-chromanone.
43. 7-(1-Phenyl-3-N-benzyl-N-methylaminopropoxy)-chromanone.
44. 6-[α-(1-Methyl-3-piperidyl)-benzyloxy]-chromanone.
45. 7-[α-(1-Methyl-3-piperidyl)-benzyloxy]-chromanone.
46. 6-[2-(1-Methyl-2-piperidyl)-ethoxy]-chromanone.
47. 7-[2-(1-Methyl-2-piperidyl)-ethoxy]-chromanone, hydrochloride, m.p. 182°–184°.
48. 6-(1,3-Dimethyl-4-hexahydroazepinyloxy)-chromanone.
49. 7-(1,3-Dimethyl-4-hexahydroazepinyloxy)-chromanone.
50. 6-(1-Phenyl-3-methylaminopropoxy)-flavanone.
51. 7-(1-Phenyl-3-methylaminopropoxy)-flavanone.
52. 6-(1-Phenyl-3-dimethylaminopropoxy)-flavanone.
53. 7-(1-Phenyl-3-dimethylaminopropoxy)-flavanone.
54. 6-(1-Phenyl-3-N-benzyl-N-methylaminopropoxy)-flavanone.
55. 7-(1-Phenyl-3-N-benzyl-N-methylaminopropoxy)-flavanone.
56. 6-[α-(1-Methyl-3-piperidyl)-benzyloxy]-flavanone.
57. 7-[α-(1-Methyl-3-piperidyl)-benzyloxy]-flavanone.
58. 6-[2-(1-Methyl-2-piperidyl)-ethoxy]-flavanone.
59. 7-[2-(1-Methyl-2-piperidyl)-ethoxy]-flavanone.
60. 6-(1,3-Dimethyl-4-hexahydroazepinyloxy)-flavanone.
61. 7-(1,3-Dimethyl-4-hexahydroazepinyloxy)-flavanone.
62. 6-(1-Phenyl-3-methylaminopropoxy)-isoflavanone.
63. 7-(1-Phenyl-3-methylaminopropoxy)-isoflavanone.
64. 6-(1-Phenyl-3-dimethylaminopropoxy)-isoflavanone.
65. 7-(1-Phenyl-3-dimethylaminopropoxy)-isoflavanone.
66. 6-(1-Phenyl-3-N-benzyl-N-methylaminopropoxy)-isoflavanone.
67. 7-(1-Phenyl-3-N-benzyl-N-methylaminopropoxy)-isoflavanone.
68. 6-[α-(1-Methyl-3-piperidyl)-benzyloxy]-isoflavanone.
69. 7-[α-(1-Methyl-3-piperidyl)-benzyloxy]-isoflavanone.
70. 6-[2-(1-Methyl-2-piperidyl)-ethoxy]-isoflavanone.
71. 7-[2-(1-Methyl-2-piperidyl)-ethoxy]-isoflavanone.
72. 6-(1,3-Dimethyl-4-hexahydroazepinyloxy)-isoflavanone.
73. 7-(1,3-Dimethyl-4-hexahydroazepinyloxy)-isoflavanone.
74. 6-(1-Phenyl-3-methylaminopropoxy)-chromone.

75. 7-(1-Phenyl-3-methylaminopropoxy)-chromone.
76. 6-(1-Phenyl-3-dimethylaminopropoxy)-chromone.
77. 7-(1-Phenyl-3-dimethylaminopropoxy)-chromone, hydrochloride, m.p. 199°.
78. 6-(1-Phenyl-3-N-benzyl-N-methylaminopropoxy)-chromone.
79. 7-(1-Phenyl-3-N-benzyl-N-methylaminopropoxy)-chromone.
80. 6-[α-(1-Methyl-3-piperidyl)-benzyloxy]-chromone.
81. 7-[α-(1-Methyl-3-piperidyl)-benzyloxy]-chromone.
82. 6-[2-(1-Methyl-2-piperidyl)-ethoxy]-chromone.
83. 7-[2-(1-Methyl-2-piperidyl)-ethoxy]-chromone.
84. 6-(1,3-Dimethyl-4-hexahydroazepinyloxy)-chromone.
85. 6-(1,3-dimethyl-4-hexahydroazepinyloxy)-chromone.
86. 5-(1-Phenyl-3-methylaminopropoxy)-flavone.
87. 6-(1-Phenyl-3-methylaminopropoxy)-flavone, Rf 0.43 (8:2 methylene chloride/triethylamine).
88. 7-(1-Phenyl-3-methylaminopropoxy)-flavone.
89. 5-(1-Phenyl-3-dimethylaminopropoxy)-flavone, m.p. 140°-141°.
90. 6-(1-Phenyl-3-dimethylaminopropoxy)-flavone, m.p. 142°-142.5°.
91. 8-(1-Phenyl-3-dimethylaminopropoxy)-flavone.
92. 5-(1-Phenyl-3-N-benzyl-N-methylamino)-flavone.
93. 6-(1-Phenyl-3-N-benzyl-N-methylamino)-flavone, m.p. 93°-94°.
94. 7-(1-Phenyl-3-N-benzyl-N-methylamino)-flavone.
95. 5-(3-Piperidyl-methoxy)-flavone.
96. 6-(3-Piperidyl-methoxy)-flavone.
97. 7-(3-Piperidyl-methoxy)-flavone.
98. 5-(α-3-Piperidyl-benzyloxy)-flavone.
99. 6-(α-3-Piperidyl-benzyloxy)-flavone.
100. 7-(α-3-Piperidyl-benzyloxy)-flavone.
101. 5-(1-Methyl-3-piperidyl-methoxy)-flavone.
102. 6-(1-Methyl-3-piperidyl-methoxy)-flavone.
103. 7-(1-Methyl-3-piperidyl-methoxy)-flavone.
104. 5-(α-1-Methyl-3-piperidyl-benzyloxy)-flavone.
105. 6-(α-1-Methyl-3-piperidyl-benzyloxy)-flavone.
106. 7-(α-1-Methyl-3-piperidyl-benzyloxy)-flavone.
107. 5-[2-(2-Piperidyl)-ethoxy]-flavone.
108. 6-[2-(2-Piperidyl)-ethoxy]-flavone.
109. 7-[2-(2-Piperidyl)-ethoxy]-flavone.
110. 5-[1-Phenyl-2-(2-piperidyl)-ethoxy]-flavone.
111. 6-[1-Phenyl-2-(2-piperidyl)-ethoxy]-flavone.
112. 7-[1-Phenyl-2-(2-piperidyl)-ethoxy]-flavone.
113. 5-[2-(1-Methyl-2-piperidyl)-ethoxy]-flavone.
114. 6-[2-(1-Methyl-2-piperidyl)-ethoxy]-flavone.
115. 7-[2-(1-Methyl-2-piperidyl)-ethoxy]-flavone.
116. 5-[1-Phenyl-2-(1-methyl-2-piperidyl)-ethoxy]-flavone.
117. 6-[1-Phenyl-2-(1-methyl-2-piperidyl)-ethoxy]-flavone.
118. 7-[1-Phenyl-2-(1-methyl-2-piperidyl)-ethoxy]-flavone.
119. 5-(4-Hexahydroazepinyloxy)-flavone.
120. 6-(4-Hexahydroazepinyloxy)-flavone.
121. 7-(4-Hexahydroazepinyloxy)-flavone.
122. 5-(1-Methyl-4-hexahydroazepinyloxy)-flavone.
123. 6-(1-Methyl-4-hexahydroazepinyloxy)-flavone.
124. 7-(1-Methyl-4-hexahydroazepinyloxy)-flavone.
125. 5-(3-Methyl-4-hexahydroazepinyloxy)-flavone.
126. 6-(3-Methyl-4-hexahydroazepinyloxy)-flavone.
127. 7-(3-Methyl-4-hexahydroazepinyloxy)-flavone.
128. 5-(1,3-Dimethyl-4-hexahydroazepinyloxy)-flavone.
129. 6-(1,3-Dimethyl-4-hexahydroazepinyloxy)-flavone.
130. 7-(1,3-Dimethyl-4-hexahydroazepinyloxy)-flavone.
131. 5-(1-Phenyl-3-methylaminopropoxy)-isoflavone.
132. 6-(1-Phenyl-3-methylaminopropoxy)-isoflavone.
133. 7-(1-Phenyl-3-methylaminopropoxy)-isoflavone, hydrochloride, m.p. 210°-211°.
134. 5-(1-Phenyl-3-dimethylaminopropoxy)-isoflavone.
135. 6-(1-Phenyl-3-dimethylaminopropoxy)-isoflavone.
136. 8-(1-Phenyl-3-dimethylaminopropoxy)-isoflavone.
137. 5-(1-Phenyl-3-N-benzyl-N-methylaminopropoxy)-isoflavone.
138. 6-(1-Phenyl-3-N-benzyl-N-methylaminopropoxy)-isoflavone.
139. 7-(1-Phenyl-3-N-benzyl-N-methylaminopropoxy)-isoflavone, m.p. 115°-118°. Hydrochloride, m.p. 210°-212°.
140. 5-(3-Piperidyl-methoxy)-isoflavone.
141. 6-(3-Piperidyl-methoxy)-isoflavone.
142. 7-(3-Piperidyl-methoxy)-isoflavone.
143. 5-(α-3-Piperidyl-benzyloxy)-isoflavone.
144. 6-(α-3-Piperidyl-benzyloxy)-isoflavone.
145. 7-(α-3-Piperidyl-benzyloxy)-isoflavone.
146. 5-(1-Methyl-3-piperidyl-methoxy)-isoflavone.
147. 6-(1-Methyl-3-piperidyl-methoxy)-isoflavone.
148. 7-(1-Methyl-3-piperidyl-methoxy)-isoflavone, hydrochloride, m.p. 257°-260°.
149. 5-(α-1-Methyl-3-piperidyl-benzyloxy)-isoflavone.
150. 6-(α-1-Methyl-3-piperidyl-benzyloxy)-isoflavone.
151. 7-(α-1-Methyl-3-piperidyl-benzyloxy)-isoflavone, hydrochloride, m.p. 143°-145°.
152. 5-[2-(2-Piperidyl)-ethoxy]-isoflavone.
153. 6-[2-(2-Piperidyl)-ethoxy]-isoflavone.
154. 7-[2-(2-Piperidyl)-ethoxy]-isoflavone.
155. 5-[1-Phenyl-2-(2-piperidyl)-ethoxy]-isoflavone.
156. 6-[1-Phenyl-2-(2-piperidyl)-ethoxy]-isoflavone.
157. 7-[1-Phenyl-2-(2-piperidyl)-ethoxy]-isoflavone.
158. 5-[2-(1-Methyl-2-piperidyl)-ethoxy]-isoflavone.
159. 6-[2-(1-Methyl-2-piperidyl)-ethoxy]-isoflavone.
160. 7-[2-(1-Methyl-2-piperidyl)-ethoxy]-isoflavone, hydrochloride, m.p. 206°-207°.
161. 5-[1-Phenyl-2-(1-methyl-2-piperidyl)-ethoxy]-isoflavone.
162. 6-[1-Phenyl-2-(1-methyl-2-piperidyl)-ethoxy]-isoflavone.
163. 7-[1-Phenyl-2-(1-methyl-2-piperidyl)-ethoxy]-isoflavone.
164. 5-(4-Hexahydroazepinyloxy)-isoflavone.
165. 6-(4-Hexahydroazepinyloxy)-isoflavone.
166. 7-(4-Hexahydroazepinyloxy)-isoflavone.
167. 5-(1-Methyl-4-hexahydroazepinyloxy)-isoflavone.
168. 6-(1-Methyl-4-hexahydroazepinyloxy)-isoflavone.
169. 7-(1-Methyl-4-hexahydroazepinyloxy)-isoflavone.
170. 5-(3-Methyl-4-hexahydroazepinyloxy)-isoflavone.
171. 6-(3-Methyl-4-hexahydroazepinyloxy)-isoflavone.
172. 7-(3-Methyl-4-hexahydroazepinyloxy)-isoflavone.
173. 5-(1,3-Dimethyl-4-hexahydroazepinyloxy)-isoflavone.
174. 6-(1,3-Dimethyl-4-hexahydroazepinyloxy)-isoflavone.
175. 7-(1,3-Dimethyl-4-hexahydroazepinyloxy)-isoflavone.
176. 5-(1-Phenyl-3-methylaminopropoxy)-1-tetralone.
177. 6-(1-Phenyl-3-methylaminopropoxy)-1-tetralone.
178. 7-(1-Phenyl-3-methylaminopropoxy)-1-tetralone.
179. 5-(1-Phenyl-3-dimethylaminopropoxy)-1-tetralone.
180. 6-(1-Phenyl-3-dimethylaminopropoxy)-1-tetralone.
181. 7-(1-Phenyl-3-dimethylaminopropoxy)-1-tetralone, hydrochloride, m.p. 167°-169°.
182. 5-(1-Phenyl-3-N-benzyl-N-methylaminopropoxy)-1-tetralone.

262. 3-Cyclopentyl-6-(1-phenyl-3-methylaminopropoxy)-chromone.
263. 3-Cyclopentyl-7-(1-phenyl-3-methylaminopropoxy)-chromone.
264. 3-Cyclopentyl-6-(1-phenyl-3-dimethylaminopropoxy)-chromone.
265. 3-Cyclopentyl-7-(1-phenyl-3-dimethylaminopropoxy)-chromone.
266. 3-Cyclopentyl-6-(1-phenyl-3-N-benzyl-N-methylaminopropoxy)-chromone.
267. 3-Cyclopentyl-7-(1-phenyl-3-N-benzyl-N-methylaminopropoxy)-chromone.
268. 3-Cyclopentyl-6-[α-1-(methyl-3-piperidyl)-benzyloxy]-chromone.
269. 3-Cyclopentyl-7-[α-1-(methyl-3-piperidyl)-benzyloxy]-chromone.
270. 3-Cyclopentyl-6-[2-(1-methyl-2-piperidyl)-ethoxy]-chromone.
271. 3-Cyclopentyl-7-[2-(1-methyl-2-piperidyl)-ethoxy]-chromone.
272. 3-Cyclopentyl-6-(1,3-dimethyl-4-hexahydroazepinyloxy)-chromone.
273. 3-Cyclopentyl-7-(1,3-dimethyl-4-hexahydroazepinyloxy)-chromone.
274. 2-Cyclohexyl-6-(1-phenyl-3-methylaminopropoxy)-chromone.
275. 2-Cyclohexyl-7-(1-phenyl-3-methylaminopropoxy)-chromone.
276. 2-Cyclohexyl-6-(1-phenyl-3-dimethylaminopropoxy)-chromone.
277. 2-Cyclohexyl-7-(1-phenyl-3-dimethylaminopropoxy)-chromone.
278. 2-Cyclohexyl-6-(1-phenyl-3-N-benzyl-N-methylaminopropoxy)-chromone.
279. 2-Cyclohexyl-7-(1-phenyl-3-N-benzyl-N-methylaminopropoxy)-chromone.
280. 2-Cyclohexyl-6-[α-(1-methyl-3-piperidyl(-benzyloxy]-chromone.
281. 2-Cyclohexyl-7-[α-(1-methyl-3-piperidyl)-benzyloxy]-chromone.
282. 2-Cyclohexyl-6-[2-(1-methyl-2-piperidyl)-ethoxy]-chromone.
283. 2-Cyclohexyl-7-[2-(1-methyl-2-piperidyl)-ethoxy]-chromone.
284. 2-Cyclohexyl-6-(1,3-dimethyl-4-hexahydroazepinyloxy)-chromone.
285. 2-Cyclohexyl-7-(1,3-dimethyl-4-hexahydroazepinyloxy)-chromone.
286. 3-Cyclohexyl-6-(1-phenyl-3-methylaminopropoxy)-chromone.
287. 3-Cyclohexyl-7-(1-phenyl-3-methylaminopropoxy)-chromone.
288. 3-Cyclohexyl-6-(1-phenyl-3-dimethylaminopropoxy)-chromone.
289. 3-Cyclohexyl-7-(1-phenyl-3-dimethylaminopropoxy)-chromone.
290. 3-Cyclohexyl-6-(1-phenyl-3-N-benzyl-N-methylaminopropoxy)-chromone.
291. 3-Cyclohexyl-7-(1-phenyl-3-N-benzyl-N-methylaminopropoxy)-chromone.
292. 3-Cyclohexyl-6-[α-(1-methyl-3-piperidyl)-benzyloxy]-chromone.
293. 3-Cyclohexyl-7-[α-(1-methyl-3-piperidyl)-benzyloxy]-chromone.
294. 3-Cyclohexyl-6-[2-(1-methyl-2-piperidyl)-ethoxy]-chromone.
295. 3-Cyclohexyl-7-[2-(1-methyl-2-piperidyl)-ethoxy]-chromone.
296. 3-Cyclohexyl-6-(1,3-dimethyl-4-hexahydroazepinyloxy)-chromone.
297. 3-Cyclohexyl-7-(1,3-dimethyl-4-hexahydroazepinyloxy)-chromone.
298. 3-Methyl-6-(1-phenyl-3-dimethylaminopropoxy)-3',4'-methylenedioxy-flavone, m.p. 74°–76°.
299. 3-Methyl-7-(1-phenyl-3-dimethylaminopropoxy)-3',4'-methylenedioxy-flavone.
300. 2-Ethyl-6-(1-phenyl-3-dimethylaminopropoxy)-isoflavone.
301. 2-Ethyl-7-(1-phenyl-3-dimethylaminopropoxy)-isoflavone, hydrochloride, m.p. 226°–228°.
302. 6-(1-Phenyl-3-dimethylaminopropoxy)-4'-fluoroisoflavone.
303. 7-(1-Phenyl-3-dimethylaminopropoxy)-4'-fluoroisoflavone, m.p. 112°–113°; hydrochloride, m.p. 234°–235°.
304. 6-(1-Phenyl-3-dimethylaminopropoxy)-4'-chloroisoflavone.
305. 7-(1-Phenyl-3-dimethylaminopropoxy)-4'-chloroisoflavone, hydrochloride, m.p. 259°–260°.
306. 6-(1-Phenyl-3-dimethylaminopropoxy)-3'-trifluoromethyl-isoflavone.
307. 7-(1-Phenyl-3-dimethylaminopropoxy)-3'-trifluoromethyl-isoflavone, hydrochloride, m.p. 174°–176°.
308. 6-(1-p-Fluorophenyl-3-dimethylaminopropoxy)-4'-fluoro-isoflavone.
309. 7-(1-p-Fluorophenyl-3-dimethylaminopropoxy)-4'-fluoro-isoflavone, m.p. 121°–123°; hydrochloride, m.p. 229°–230°.
310. 6-(1-p-Fluorophenyl-3-dimethylaminopropoxy)-4'-chloro-isoflavone.
311. 7-(1-p-Fluorophenyl-3-dimethylaminopropoxy)-4'-chloro-isoflavone, hydrochloride, m.p. 213°–215°.
312. 6-(1-p-Fluorophenyl-3-dimethylaminopropoxy)-3'-trifluoromethyl-isoflavone.
313. 7-(1-p-Fluorophenyl-3-dimethylaminopropoxy)-3'-trifluoromethyl-isoflavone, hydrochloride, m.p. 174°–176°.

EXAMPLE 314

23.8 g of 7-hydroxyisoflavone is dissolved in 500 ml of absolute toluene, 7.1 ml of thallium-(I) ethylate are added and the mixture is stirred for 1 hour at 20°. After evaporation, the residue is dissolved in 100 ml of absolute acetonitrile, 20 g of 1-chloro-1-phenyl-3-dimethylaminopropane is added and the mixture is boiled for 3 hours while stirring and is evaporated. Working up in the customary manner gives 7-(1-phenyl-3-dimethylaminopropoxy)-isoflavone. M.p. 128°–130°.

EXAMPLE 315

2.7 g of azodicarboxylic acid ethyl ester is dissolved in 25 ml of THF, 4 g of triphenylphosphine is added, while cooling and stirring; a solution of 2 g of 1-chloro-1-phenyl-3-dimethylaminopropane in 15 ml of THF is then added dropwise, followed by a solution of 2.38 g of 7-hydroxyisoflavone in 10 ml of THF and the mixture is stirred for 2 hours at 0°. After being allowed to stand overnight at 20°, the mixture is worked up in the customary manner. This gives 7-(1-phenyl-3-dimethylaminopropoxy)-isoflavone. M.p. 128°–130°.

EXAMPLE 316

200 ml of 50% aqueous sodium hydroxide solution and 1 g of triethylbenzylammonium chloride are added to a solution of 23.8 g of 7-hydroxyisoflavone in 100 ml 183. 6-(1-Phenyl-3-N-benzyl-N-methylaminopropoxy)-1-tetralone, Rf 0.4 (ethyl acetate).
184. 7-(1-Phenyl-3-N-benzyl-N-methylaminopropoxy)-1-tetralone, hydrochloride, m.p. 178°-180°.
185. 5-(3-Piperidyl-methoxy)-1-tetralone.
186. 6-(3-Piperidyl-methoxy)-1-tetralone.
187. 7-(3-Piperidyl-methoxy)-1-tetralone.
188. 5-(α-3-Piperidyl-benzyloxy)-1-tetralone.
189. 6-(α-3-Piperidyl-benzyloxy)-1-tetralone.
190. 7-(α-3-Piperidyl-benzyloxy)-1-tetralone.
191. 5-(1-Methyl-3-piperidyl-methoxy)-1-tetralone.
192. 6-(1-Methyl-3-piperidyl-methoxy)-1-tetralone.
193. 7-(1-Methyl-3-piperidyl-methoxy)-1-tetralone.
194. 5-(α-1-Methyl-3-piperidyl-benzyloxy)-1-tetralone.
195. 6-(α-1-Methyl-3-piperidyl-benzyloxy)-1-tetralone.
196. 7-(α-1-Methyl-3-piperidyl-benzyloxy)-1-tetralone.
197. 5-[2-(2-Piperidyl)-ethoxy]-1-tetralone.
198. 6-[2-(2-Piperidyl)-ethoxy]-1-tetralone.
199. 7-[2-(2-Piperidyl)ethoxy]-1-tetralone.
200. 5-[1-Phenyl-2-(2-piperidyl)-ethoxy]-1-tetralone.
201. 6-[1-Phenyl-2-(2-piperidyl)-ethoxy]-1-tetralone.
202. 7-[1-Phenyl-2-(2-piperidyl)-ethoxy]-1-tetralone.
203. 5-[2-(1-Methyl-2-piperidyl)-ethoxy]-1-tetralone.
204. 6-[2-(1-Methyl-2-piperidyl)-ethoxy]-1-tetralone.
205. 7-[2-(1-Methyl-2-piperidyl)-ethoxy]-1-tetralone, hydrochloride, m.p. 188°-190°.
206. 5-[1-Phenyl-2-(1-methyl-2-piperidyl)-ethoxy]-1-tetralone.
207. 6-[1-Phenyl-2-(1-methyl-2-piperidyl)-ethoxy]-1-tetralone.
208. 7-[1-Phenyl-2-(1-methyl-2-piperidyl)-ethoxy]-1-tetralone.
209. 5-(4-Hexahydroazepinyloxy)-1-tetralone.
210. 6-(4-Hexahydroazepinyloxy)-1-tetralone.
211. 7-(4-Hexahydroazepinyloxy)-1-tetralone.
212. 5-(1-Methyl-4-hexahydroazepinyloxy)-1-tetralone.
213. 6-(1-Methyl-4-hexahydroazepinyloxy)-1-tetralone.
214. 7-(1-Methyl-4-hexahydroazepinyloxy)-1-tetralone.
215. 5-(3-Methyl-4-hexahydroazepinyloxy)-1-tetralone.
216. 6-(3-Methyl-4-hexahydroazepinyloxy)-1-tetralone.
217. 7-(3-Methyl-4-hexahydroazepinyloxy)-1-tetralone.
218. 5-(1,3-Dimethyl-4-hexahydroazepinyloxy)-1-tetralone.
219. 6-(1,3-Dimethyl-4-hexahydroazepinyloxy)-1-tetralone.
220. 7-(1,3-Dimethyl-4-hexahydroazepinyloxy)-1-tetralone.

EXAMPLES 221 TO 313

The following are obtained analogously to Example 1 from the corresponding Na phenolates and the corresponding chloroamines or bromoamines:

221. 6-(1-Cyclopropyl-3-dimethylaminopropoxy)-isoflavone.
222. 7-(1-Cyclopropyl-3-dimethylaminopropoxy)-isoflavone.
223. 6-(1-p-Fluorophenyl-3-dimethylaminopropoxy)-isoflavone.
224. 7-(1-p-Fluorophenyl-3-dimethylaminopropoxy)-isoflavone, hydrochloride, m.p. 217°.
225. 6-(1-p-Chlorophenyl-3-dimethylaminopropoxy)-isoflavone.
226. 7-(1-p-Chlorophenyl-3-dimethylaminopropoxy)-isoflavone, hydrochloride, m.p. 247°.
227. 6-(1-p-Methoxyphenyl-3-dimethylaminopropoxy)-isoflavone.
228. 7-(1-p-Methoxyphenyl-3-dimethylaminopropoxy)-isoflavone, m.p. 111°-113°.
229. 6-(1-p-Methylthiophenyl-3-dimethylaminopropoxy)-iso-flavone.
230. 7-(1-p-Methylthiophenyl-3-dimethylaminopropoxy)-isoflavone.
231. 6-(1-Phenyl-3-dimethylaminopropoxy)-4'-methoxyflavan, hydrochloride, m.p. 166°-168°.
232. 7-(1-Phenyl-3-dimethylaminopropoxy)-4'-methoxyflavan.
233. 3-Methyl-6-(1-phenyl-3-dimethylaminopropoxy)-3',4'-methylenedioxy-flavanone, hydrochloride, m.p. 80°-120°.
234. 3-Methyl-7-(1-phenyl-3-dimethylaminopropoxy)-3',4'-methylenedioxy-flavanone.
235. cis-3-Ethyl-6-(1-phenyl-3-dimethylaminopropoxy)-4'-methoxy-flavanone, Rf 0.55.
236. trans-3-Ethyl-6-(1-phenyl-3-dimethylaminopropoxy)-4'-methoxy-flavanone, Rf 0.57.
237. cis-3-n-Propyl-6-(1-phenyl-3-dimethylaminopropoxy)-flavanone, Rf 0.44.
237. 3-tert.-Butyl-6-(1-phenyl-3-methylaminopropoxy)-chromone.
239. 3-tert.-Butyl-7-(1-phenyl-3-methylaminopropoxy)-chromone.
240. 3-tert.-Butyl-6-(1-phenyl-3-dimethylaminopropoxy)-chromone.
241. 3-tert.-Butyl-7-(1-phenyl-3-dimethylaminopropoxy)-chromone.
242. 3-tert.-Butyl-6-(1-phenyl-3-N-benzyl-N-methylaminopropoxy)-chromone.
243. 3-tert.-Butyl-7-(1-phenyl-3-N-benzyl-N-methylaminopropoxy)-chromone.
244. 3-tert.-Butyl-6-[α-(1-methyl-3-piperidyl)-benzyloxy]-chromone.
245. 3-tert.-Butyl-7-[α-(1-methyl-3-piperidyl)-benzyloxy]-chromone.
246. 3-tert.-Butyl-6-[2-(1-methyl-2-piperidyl)ethoxy]-chromone.
247. 3-tert.-Butyl-7-[2-(1-methyl-2-piperidyl)-ethoxy]-chromone.
248. 3-tert.-Butyl-6-(1,3-dimethyl-4-hexahydroazepinyloxy)-chromone.
249. 3-tert.-Butyl-7-(1,3-dimethyl-4-hexahydroazepinyloxy)-chromone.
250. 2-Cyclopentyl-6-(1-phenyl-3-methylaminopropoxy)-chromone.
251. 2-Cyclopentyl-7-(1-phenyl-3-methylaminopropoxy)-chromone.
252. 2-cyclopentyl-6-(1-phenyl-3-dimethylaminopropoxy)-chromone.
253. 2-Cyclopentyl-7-(1-phenyl-3-dimethylaminopropoxy)-chromone.
254. 2-Cyclopentyl-6-(1-phenyl-3-N-benzyl-N-methylaminopropoxy)-chromone.
255. 2-Cyclopentyl-7-(1-phenyl-3-N-benzyl-N-methylaminopropoxy)-chromone.
256. 2-Cyclopentyl-6-[α-(1-methyl-3-piperidyl)-benzyloxy]-chromone.
257. 2-Cyclopentyl-7-[α-(1-methyl-3-piperidyl)-benzyloxy]-chromone.
258. 2-Cyclopentyl-6-[2-(1-methyl-2-piperidyl)-ethoxy]-chromone.
259. 2-Cyclopentyl-7-[2-(1-methyl-2-piperidyl)-ethoxy]-chromone.
260. 2-Cyclopentyl-6-(1,3-dimethyl-4-hexahydroazepinyloxy)-chromone.
261. 2-Cyclopentyl-7-(1,3-dimethyl-4-hexahydroazepinyloxy)-chromone.

of CH₂Cl₂, 20 g of 1-chloro-1-phenyl-3-dimethylaminopropane is added dropwise while stirring and stirring is continued for a further hour. Working up in the customary manner gives 7-(1-phenyl-3-dimethylaminopropoxy)-isoflavone. M.p. 128°–130°.

EXAMPLE 317

A solution of 20 g of 7-(1-phenyl-3-N-benzyl-N-methylaminopropoxy)-isoflavone in 400 ml of methanol is hydrogenated over 3 g of 5% Pd-on-C at 20° and 1 atmosphere until absorption of hydrogen ceases. The mixture is filtered and evaporated to give 7-(1-phenyl-3-methylaminopropoxy)-isoflavone, hydrochloride, m.p. 210°–211°.

EXAMPLE 318

30 g of formic acid, is added dropwise to 38.5 g of 7-(1phenyl-3-methylaminopropoxy)-isoflavone, while stirring and cooling, and 7 g of 25% formaldehyde solution is then added dropwise at 20°. The mixture is heated on a waterbath until evolution of gas ceases and is cooled, poured onto ice and worked up in the customary manner to give 7-(1-phenyl-3-dimethylaminopropoxy)-isoflavone. M.p. 128°–130°.

EXAMPLE 319

12 g of allyl bromide and 26 g of anhydrous potassium carbonate are added to a solution of 38.5 g of 7-(1-phenyl-3-methylaminopropoxy)-isoflavone in 1 L of absolute toluene and the mixture is boiled for 20 hours, cooled, poured into water and worked up in the customary manner to give 7-(1-phenyl-3-N-allyl-N-methylaminopropoxy)-isoflavone. Hydrochloride, m.p. 192°–194°.

EXAMPLES 320 TO 326

The following are obtained analogously to Example 319 using allyl bromide, n-butyl iodide, cyclopropylmethyl chloride or benzyl bromide:
320. 6-(1-Phenyl-3-N-allyl-N-methylaminopropoxy)-isoflavone.
321. 6-(1-Phenyl-3-N-n-butyl-N-methylaminopropoxy)-isoflavone.
322. 7-(1-Phenyl-3-N-n-butyl-N-methylaminopropoxy)-isoflavone.
323. 6-(1-Phenyl-3-N-cyclopropylmethyl-N-methylaminopropoxy)-isoflavone.
324. 7-(1-Phenyl-3-N-cyclopropylmethyl-N-methylaminopropoxy)-isoflavone, hydrochloride, m.p. 225°–227°.
325. 6-(1-Phenyl-3-N-benzyl-N-methylaminopropoxy)-isoflavone.
326. 7-(1-Phenyl-3-N-benzyl-N-methylaminopropoxy)-isoflavone.

EXAMPLES 327 TO 331

The following are obtained analogously to Example 1 from the corresponding Na phenolates and the corresponding basic chlorides:
327. 6-(1-Cyclopropyl-3-methylaminopropoxy)-flavone, Rf 0.45 (8:2 chloroform/triethylamine).
328. 6-(1-Phenyl-3-dimethylaminopropoxy)-4'-methoxyflavone, m.p. 125°–127°.
329. 6-(1-Phenyl-3-dimethylaminopropoxy)-3',4'-methylenedioxy-flavone, m.p. 159°–160°.
330. 7-(1-Cyclopropyl-3-methylaminopropoxy)-chroman, Rf 0.24 (methanol).
331. 7-(1-Cyclopropyl-3-dimethylaminopropoxy)-chroman, Rf 0.74 (8:2 chloroform/triethylamine).

The following examples relate to pharmaceutical formulations containing amines of Formula I or their acid addition salts.

EXAMPLE A: TABLETS

A mixture of 1 kg of 7-(1-phenyl-3-dimethylaminopropoxy)-isoflavone hydrochloride, 4 kg of lactose, 1.2 kg of potato starch, 0.2 kg of talc and 0.1 kg of magnesium stearate is compressed in a customary manner to give tablets, in such a way that each tablet contains 10 mg of active compound.

EXAMPLE B: DRAGEES

Tablets are compressed analogously to Example A and are then coated in a customary manner with a coating consisting of sucrose, potato starch, talc, tragacanth and colorant.

EXAMPLE C: CAPSULES 2 kg of 7-(1-phenyl-3-dimethylaminopropoxy)-isoflavone hydrochloride is filled into hard gelatine capsules in a customary manner in such a way that each capsule contains 20 mg of the active compound.

EXAMPLE D: AMPOULES

A solution of 1 kg of 7-(1-phenyl-3-dimethylaminopropoxy)-isoflavone hydrochloride in 30 L of twice-distilled water is filtered under sterile conditions and filled into ampoules, which are lyophilized under sterile conditions and sealed under sterile conditions. Each ampoule contains 10 mg of active compound.

Tablets, dragees, capsules and ampoules containing one or more of the remaining active compounds of Formula I and/or their physiologically acceptable acid addition salts can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

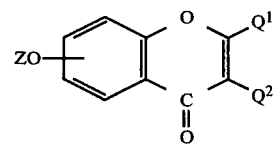

wherein Z is 1-$R^2$-3-$R^4$-4-hexahydroazepinyl;
$R^2$ is H, alkyl of 1–4 C atoms, alkenyl of 2–4 C atoms, cycloalkylalkyl of 4–8 C atoms or benzyl;
$R^4$ is H or alkyl of 1–4 C atoms;
$Q^1$ and $Q^2$ are independently each H, alkyl of 1–4 C atoms, cycloalkyl or alkylcycloalkyl each of 3–6 total C atoms or Ar;
Ar is phenyl or phenyl substituted by F, Cl, alkoxy or alkylthio, each of 1–4 C atoms, methylenedioxy or $CF_3$;

or a physiologically acceptable acid addition salt thereof.

2. A pharmaceutical composition comprising an antidepressantly effective amount of a compound of claim 1 and a pharmaceutically acceptable carrier.

3. A composition of claim 2 containing 2-500 mg of the antidepressantly active compound.

4. A method of treating depression in a patient in need of such treatment comprising administering to the patient an antidepressantly effective amount of a compound of claim 1.

* * * * *